United States Patent
Weiss et al.

(10) Patent No.: US 10,632,203 B2
(45) Date of Patent: Apr. 28, 2020

(54) SILYLATED BIOMOLECULE-BASED HYDROGEL FOR CULTURING CARDIOMYOCYTES AND STEM CELLS, AND USE OF THE HYDROGEL THEREOF FOR TREATING HEART FAILURE

(71) Applicants: Pierre Weiss, Nantes (FR); Eva Mathieu, Nantes (FR); Jerome Guicheux, Nantes (FR); Patricia Lemarchand, Nantes (FR)

(72) Inventors: Pierre Weiss, Nantes (FR); Eva Mathieu, Nantes (FR); Jerome Guicheux, Nantes (FR); Patricia Lemarchand, Nantes (FR)

(73) Assignees: INSERM (INSTITUT NATIONAL DE LA SANTÉ ET DE LA RECHERCHE MÉDICALE), Paris (FR); UNIVERSITE DE NANTES, Nantes (FR); Chu Nantes, Nantes (FR)

( * ) Notice: Subject to any disclaimer, the term of this patent is extended or adjusted under 35 U.S.C. 154(b) by 0 days.

(21) Appl. No.: 15/949,509

(22) Filed: Apr. 10, 2018

(65) Prior Publication Data
US 2018/0221493 A1 Aug. 9, 2018

Related U.S. Application Data

(62) Division of application No. 14/123,286, filed as application No. PCT/EP2012/060496 on Jun. 4, 2012, now Pat. No. 9,968,681.

(30) Foreign Application Priority Data

Jun. 3, 2011 (EP) .................... 11305683

(51) Int. Cl.
| | |
|---|---|
| A61K 47/38 | (2006.01) |
| C12N 5/00 | (2006.01) |
| C12N 5/077 | (2010.01) |
| A61K 35/34 | (2015.01) |
| A61K 35/28 | (2015.01) |
| A61K 35/12 | (2015.01) |

(52) U.S. Cl.
CPC ............ *A61K 47/38* (2013.01); *A61K 35/28* (2013.01); *A61K 35/34* (2013.01); *C12N 5/0068* (2013.01); *C12N 5/0657* (2013.01); *A61K 2035/124* (2013.01); *C12N 2533/20* (2013.01); *C12N 2533/72* (2013.01); *C12N 2533/78* (2013.01)

(58) Field of Classification Search
None
See application file for complete search history.

(56) References Cited

U.S. PATENT DOCUMENTS

| 7,569,385 B2 | 8/2009 | Haas |
| 9,285,360 B2 | 3/2016 | Weiss |
| 2009/0169521 A1 | 7/2009 | Levenberg |

FOREIGN PATENT DOCUMENTS

| EP | 1 529 543 A1 | 5/2005 |
| WO | 2010/036800 A1 | 4/2010 |

OTHER PUBLICATIONS

Merceron et al., "The effect of two and three dimensional cell culture on the chondrogenic potential of human adipose-derived mesenchymal stem cells after subcutaneous transplantation with an injectable hydrogel", Cell Transplantation, Feb. 3, 2011.
Vinatier et al., "A silanized hydroxypropyl methylcellulose hydrogel for the three-dimensional culture of chondrocytes", Biomaterials, Nov. 1, 2005, pp. 6643-6651, vol. 26, No. 33, Elsevier Science Publishers.
Vinatier et al., "An injectable cellulose-based hydrogel for the transfer of autologous nasal chondrocytes in articular cartilage defects", Biotechnology and Bioengineering, Mar. 1, 2009, pp. 1259-1267, vol. 102, No. 4.
Rederstorff et al., "An in vitro study of two GAG-like marine polysaccharides incorporated into injectable hydrogels for bone and cartilage tissue engineering", ACTA Biomaterialia, May 1, 2011, pp. 2119-2130, vol. 7, No. 5, Elsevier, Amsterdam, NL.
Choi et al., "Differentiation of human adipose-derived stem cells into beating cardiomyocytes", Journal of Cellular and Molecular Medicine, Apr. 1, 2010, pp. 878-889, vol. 14, No. 4.
Daculsi et al., "Developments in injectable multiphasic biomaterials. The performance of microporous biphasic calcium phosphate granules and hydrogels", Journal of Materials Science: Materials in Medicine, Nov. 1, 2009, pp. 855-861, vol. 21, No. 3, Kluwer Academic Publishers, BO.
Gaustad et al.; "Differentiation of human adipose tissue stem cells using extracts of rat cardiomyocytes"; Biochemical and Biophysical Research Communications, 314.2 (2004), pp. 420-427.
Xu et al.; "Mesenchymal stem cells from adult human bone marrow differentiate into a cardiomyocyte phenotype in vitro"; Experimental Biology and Medicine 229.7 (2004), pp. 623-631.
Li et al.; "Hydrogels for cardiac tissue engineering"; Polymers 3.2 (2011), pp. 740-761.

(Continued)

*Primary Examiner* — Robert J Yamasaki
(74) *Attorney, Agent, or Firm* — W & C IP

(57) ABSTRACT

The present invention relates to the use of an hydrogel comprising silylated biomolecule for the three-dimensional culture of cardiomyocytes or stem cells which are able to differentiate into cardiomyocytes, and to an aqueous composition comprising i) cardiomyocytes or stem cells which are able to differentiate into cardiomyocytes, and ii) a hydrogel comprising silylated biomolecule, for use for treating heart failure, in particular heart failure following myocardial infarction.

4 Claims, 7 Drawing Sheets

(56) References Cited

OTHER PUBLICATIONS

Zhang et al.; "Artificial matrix helps neonatal cardiomyocytes restore injured myocardium in rats"; Artificial Organs 30.2 (2006), pp. 86-93.
Yeo et al.; "Photocrosslinkable hydrogel for myocyte cell culture and injection"; Journal of Biomedical Materials Research Part B: Applied Biomaterials 81.2 (2007), pp. 312-322.

SILYLATED BIOMOLECULE-BASED HYDROGEL FOR CULTURING CARDIOMYOCYTES AND STEM CELLS, AND USE OF THE HYDROGEL THEREOF FOR TREATING HEART FAILURE

CROSS-REFERENCE TO RELATED APPLICATIONS

This application is a divisional application of U.S. Ser. No. 14/123,286 filed Feb. 20, 2014, now U.S. Pat. No. 9,968,681, which itself was a national stage filing under Rule 371 form PCT/EP2012/060496 filed Jun. 4, 2012, which claimed priority to European Application 11305683.2 filed Jun. 3 2011.

The present invention relates to the use of an hydrogel comprising silylated biomolecule for the three-dimensional culture of cardiomyocytes or stem cells which are able to differentiate into cardiomyocytes, and to an aqueous composition comprising i) cardiomyocytes or stem cells which are able to differentiate into cardiomyocytes, and ii) a hydrogel comprising silylated biomolecule, for use for treating heart failure, in particular heart failure following myocardial infarction.

BACKGROUND OF THE INVENTION

Heart disease, especially myocardial infarction, is a leading cause of morbidity and mortality worldwide. Myocardial infarction is an absolute medical emergency whose incidence remains high with 120,000 cases per year in France. According to WHO data, on 50 million annual deaths worldwide, ischemic heart disease are the leading cause of death with 7.2 million deaths from coronary heart diseases. In France, MI prognosis remains poor, (10 to 12% of total annual mortality in adults). In addition, a significant morbidity and socio-economic should be also considered. Following MI, left ventricular remodeling includes early and progressive extracellular matrix degradation, infarct zone expansion, scar thinning, and eventually transition to heart failure (Cohn, et al., 2000; Jugdutt, 2003).

Current antiremodeling therapies are clearly limited, because many ventricles continue to enlarge (Bolognese et al., 2007; Savoye et al., 2006) and morbidity and mortality remain high (Verma et al., 2008). Pharmacological treatments currently available can only delay the progression to end-stage heart failure.

Heart transplantation remains the most effective management of the most severely affected patients, but the shortage of donor organs and complications associated with this intervention limits this approach. Further, lifelong immune suppression often causes serious complications.

Because the dominant cause of heart failure is loss of myocardium as a result of infarction and the limited regeneration potential of cardiomyocytes in mammals, cell therapy may provide a novel therapeutic option to modify left ventricular remodeling processes and prevent post-infarction heart failure. Thus, in recent years, the possibility of using cell transplantation for cardiac repairs has become the focus of intense research. Multiple cell types have been considered for such therapies, including skeletal myoblasts, bone marrow-derived haematopoietic stem cells, mesenchymal stem cells, intrinsic cardiac stem cells (CSCs), embryonic stem cells (ESCs) and induced pluripotent stem (iPS) cells.

Conventional administration techniques use intramyocardial injections of suspended cells in culture medium. However, this technique is plagued by limited cell retention and survival. Several studies showed that more than 80%-90% of grafted cells die within 72 hours after injection into myocardium (Toma et al., Circulation, 105: 93-98, 2002; Maurel et al., Transplantation, 80: 660-665, 2005). Further, it was reported that approximately 90% of the cells delivered through a needle were lost to the circulation or leaked out of the injection site (Leor et al., Circulation, 102: 11156-61, 2000).

In addition, cell-seeded grafts have been proposed for in vitro cardiac tissue growth and subsequent in vivo transplantation. These grafts can consist of embryonic or neonatal cardiomyocytes seeded in three-dimensional scaffolds; the cardiac myocytes cultured in these scaffolds can spatially organize and differentiate into myocardium-like 3-dimensional tissue. These results suggest that cell therapy and tissue engineering of myocardium have potential for myocardial regeneration or replacement. However, current approaches to cardiac regeneration face important challenges. Recipient ischemic tissue may be inadequate for donor cell retention in sufficient quantity to allow for the desired effect, because the survival of cells from any source implanted in the myocardium varies between 1% and 10%. Also, nonspecific delivery of donor cells to other body sites constitutes an unwanted potential side effect.

A particularly useful approach to cardiac regeneration would be a method that could employ injection into the injured area in a manner similar to cell injection therapy (rather than surgical implantation of myocardium-like volume) and that would provide a suitable growth environment for cardiomyocytes.

In recent years, several types of biomaterials, mainly natural proteins, were used in the injectable cardiac tissue engineering, such as fibrin, alginate, matrigel, collagen and chitosan (see for review Wang et al., J. Cell. Mol. Med., 14(5): 1044-1055, 2010).

However, use of natural materials extracted from biological samples is associated with a major risk of microbial transmission, essentially virus transmission. Drawbacks associated with natural materials have prompted the inventors to develop synthetic materials for injectable cardiac tissue engineering.

The inventors had previously developed a silylated hydrogel as a culture matrix for three-dimensional culture of chondrocytes for use for regenerating in vivo cartilaginous tissues (application US 2007/0212389).

However, in view of the great difference between cartilaginous tissue and cardiac tissue, respectively hard and soft tissues, and of the physiological differences between chondrocytes and cardiomyocytes, the latter needing to retain contractile ability to be functional, it was not expected that silylated hydrogel is also usable for culturing functional cardiomyocytes.

DESCRIPTION OF THE INVENTION

The inventors have now found that a reticulated hydrogel comprising a silylated biomolecule able to form a pH-dependent self-reticulating hydrogel can be used for the three-dimensional culture of cardiomyocytes, or of stem cells which are able to differentiate into cardiomyocytes.

The inventors have also shown that this hydrogel comprising stem cells, in particular mesenchymal stem cells, once injected into the heart, in particular into left ventricle, has a cardioprotective effect.

The inventors have also shown the tolerability and cytocompatibility of silylated biomolecule hydrogel, in particular Si-HPMC hydrogel, with cardiomyocytes, and its ability to maintain a cardiomyocyte phenotype and to allow physiological cardiomyocyte contractility. Results in vivo also showed that cells maintained their viability and that hydrogel of the invention had no adverse effect on cardiac tissue.

The inventors have also demonstrated that use of hydrogel comprising a silylated biomolecule comprising stem cells able to differentiate into cardiomyocytes, or mesenchymal stem cells, rapidly improves cardidac function and preserves long term cardiac function. Further, transplantation of hydrogel comprising a silylated biomolecule comprising stem cells decreases the infarct expansion, which indicates that this combination is capable of preventing negative left ventricular remodeling after myocardial infarction.

Therefore, a first aspect of the present invention relates to the use of a hydrogel comprising silylated biomolecules, for the three-dimensional culture of cardiomyocytes or stem cells which are able to differentiate into cardiomyocytes.

In a preferred embodiment, the cultured cells are cardiomyocytes.

Preferably, the hydrogel comprising silylated biomolecules is able to form a pH-dependent self-reticulating hydrogel at physiological pH (i.e. with a pH value from about 7.2 to about 7.6).

The above use of the invention may be, for instance, an in vitro or ex vivo use.

A second aspect of the invention is a method of culturing cardiomyocytes or stem cells which are able to differentiate into cardiomyocytes, comprising the ex vivo mixing of said cells with a hydrogel comprising silylated biomolecules at an appropriate pH for forming the hydrogel. Preferably, the pH of the hydrogel comprising silylated biomolecules is a physiological pH (pH from about 7.2 to about 7.6). In a preferred embodiment, the cultured cells are cardiomyocytes.

A third aspect of the invention relates to a method of treating heart failure, in particular heart failure following myocardial infarction, including administration by injection into myocardium of an aqueous composition, preferably at a physiological pH (pH from about 7.2 to about 7.6), said composition comprising:

i) cardiomyocytes or stem cells which are able to differentiate into cardiomyocytes; and ii) a hydrogel solution, preferably at physiological pH (pH from about 7.2 to about 7.6), comprising silylated biomolecule.

A fourth aspect of the invention concerns an aqueous composition, preferably at a physiological pH (pH from about 7.2 to about 7.6) which comprises:

i) cardiomyocytes or stem cells which are able to differentiate into cardiomyocytes; and ii) a hydrogel solution, preferably at physiological pH (pH from about 7.2 to about 7.6), comprising silylated biomolecule;

for use for treating heart failure, in particular heart failure following myocardial infarction.

To carry out the method of treating heart failure and medical application according to the third and fourth aspects of the invention, the aqueous composition will preferably be injectable (i.e. liquid or at least semi-liquid form, and not totally gelified). The man skilled in the art can easily determine the appropriate moment when said aqueous composition is suitable for being administrated (or used for treating).

Preferably, the aqueous composition is administered (or used for treating) from a few seconds to 15 minutes after the aqueous solution comprising silylated biomolecule is mixed with a buffering solution. The pH of the final aqueous solution which is administered preferably has a physiological value (i.e. pH from about 7.2 to about 7.6). Preferably, cardiomyocytes or stem cells are added when the aqueous solution of point (ii) above reaches a pH from 7.2 to 7.6.

Once injected into myocardium, viscosity of the aqueous composition gradually increases until formation of a hydrogel into which cardiomyocytes or stem cells which are able to differentiate into cardiomyocytes are present.

The aqueous composition is injected into myocardium, in particular into the left ventricle, and preferably into the sites along the infarcted area. The infarcted area can be identified by the surface scar and wall motion akinesis as described by Takagawa et al. (J. Appl. Physiol., 102(6): 2104-11, 2007, PMID: 17347379).

The injection may be carried out using a system comprising sterilizable syringe and needle, and connection pieces provided with single-use plungers.

In a preferred embodiment of the method of treating heart failure and medical application according to the third and fourth aspects of the invention, stem cells of the aqueous composition are mesenchymal stem cells. The beneficial effects of mesenchymal stem cell grafts are known to be related in part to their paracrine activity. Mesenchymal stem cells secrete angiogenic, antiapoptotic, and anti-inflammatory cytokines that contribute to the recovery of cardiac function and significantly decrease fibrosis in the heart (Aggarwal S and Pittenger M F., Blood, 105: 1815-1822, 2005; Tse W T et al., Transplantation, 75: 389-397, 2003; Nagaya N. et al., Circulation, 112: 1128-1135, 2005; and Li L, Zhang Y, Li Y, Yu B, Xu Y, et al., Transpl. Int., 21: 1181-1189, 2008).

A fifth aspect of the invention relates to a kit for obtaining an aqueous composition that is usable in a method of treating heart failure, in particular heart failure following myocardial infarction, and in the medical application of the invention described above.

The Kit of the fifth aspect of the invention may comprise i) cardiomyocytes or stem cells which are able to differentiate into cardiomyocytes, and ii) a hydrogel solution which comprises silylated biomolecule. Preferably, the kit comprises Mesenchymal stem cells.

The kit of the fifth aspect of the invention may also comprise instructions for the use of said kit in preparing a composition at physiological pH (pH from about 7.2 to about 7.6) comprising:

i) cardiomyocytes or stem cells which are able to differentiate into cardiomyocytes; and ii) a hydrogel solution comprising silylated biomolecule;

said composition being intended to be injected into myocardium, in particular left ventricle.

A sixth aspect of the invention relates to a kit for the three-dimensional culture of cardiomyocytes or stem cells which are able to differentiate into cardiomyocytes.

The kit of the sixth aspect of the invention may comprise i) cardiomyocytes or stem cells which are able to differentiate into cardiomyocytes, and ii) a hydrogel solution which comprises silylated biomolecule. Preferably, the kit comprises cardiomyocytes or Mesenchymal stem cells, more preferably cardiomyocytes.

The kit of the sixth aspect of the invention may also comprise instructions for the use of said kit in culturing cardiomyocytes or stem cells which are able to differentiate into cardiomyocytes in three-dimensional culture Preferably, the hydrogel solution (ii) of the kits of the fifth and sixth aspects of the invention has a pH higher than 12, and hence is in liquid form (the silylated biomolecule comprised in the hydrogel solution is stable in aqueous solution at a pH greater than or equal to approximately 12.4).

Cardiomyocytes or stem cells can be provided in both kits in a culture medium. The culture media suitable for culturing such cells are well known to a person skilled in the art, for instance Dulbecco'S modified Eagle medium (DMEM), alpha Modified Eagle medium (α-MEM). Alternatively, the cells can be provided as frozen cells.

Both kits may further comprise a buffering solution which may be used to produce a hydrogel solution ii) with a physiological pH. A suitable buffering solution may be any solution of pH 4 or below which once mixed with the hydrogel solution in aqueous solution allow to obtain a final aqueous solution at physiological pH (i.e. with a pH value from 7.2 to 7.6, preferably 7.4) and at physiological osmotic pressure (i.e. about 300 mOsm/L). Examples of such a buffering solution are HCl, HEPES and TRIS.

In a preferred embodiment of the first, second and sixth aspects of the invention, the hydrogel has the following rheological characteristics at a pH value of 7.4 (after 3 weeks of reticulation):
 a compressive modulus at 5% stress from 220 to 15 000 Pa;
 a storage modulus (G') from 235 to 10 000 Pa;
 a loss modulus (G") from 29 to 1000 Pa;
 a gel point from 5 to 45 minutes.

More preferably, the hydrogel of the first, second and sixth aspects of the invention contains 1 to 3% w/v of si-HPMC (before addition of cells).

Advantageously, the hydrogel contains 2% w/v of si-HPMC and has the following rheological characteristics at a pH value of 7.4 (after 3 weeks of reticulation):
 a compressive modulus at 5% stress from 1600 to 2600 Pa;
 a storage modulus (G') from 800 to 2500 Pa;
 a loss modulus (G") from 30 to 110 Pa;
 a gel point from 20 to 30 minutes.

The inventors have found that a hydrogel with the above recited rheological characteristics is particularly adapted to cardyomyocyte culture since such a hydrogel allows maintenance of cardiomyocyte contractile activity in three-dimensional culture.

In a preferred embodiment of the third, fourth and fifth aspects of the invention, the hydrogel has the following rheological characteristics at a pH value of 7.4 (after 3 weeks of reticulation):
 a compressive modulus at 5% stress from 220 to 430 Pa;
 a storage modulus (G') from 235 to 450 Pa;
 a loss modulus (G") from 29 to 60 Pa;
 a gel point from 23.8 to 30.6 minutes.

When the hydrogel is made of si-HPMC, such rheological characteristics are obtained when the final aqueous solution (i.e. after addition of the buffering solution) contains 1.5% w/v of si-HPMC (before addition of cells).

Preferably, the hydrogel contains 0.8 to 1.5% w/v of si-HPMC (before addition of cells)

The inventors have found that a hydrogel with the above recited rheological characteristics does not alter MSC viability or activity, and that injection such a hydrogel load with MSCs in the heart directly after MI leads to cardiac function and LV remodeling preservation.

The rheological measurements are carried out after 3 weeks of reticulation, at 25° C., on a rotational rheometer (Rheostress 300, ThermoHaake®, Germany) using a coni-cylindrical geometry with a diameter of 60 mm and a cone angle of 1°. A multiwave procedure with 3 frequencies 1, 3.2 and 10 Htz is used, and the imposed stress is 1 Pa. Oscillation tests measuring storage modulus (G') and loss modulus (G") are performed to study the self-setting process and gel point. The gel points are given as the time taken for the liquid (G">G') to turn into a solid (G'>G"). They are determined according to a derived percolation theory as disclosed by Fatimi et al. (Acta Biomater, 5: 3423-3432). Compressive modulus of scaffold is measured using a TA HD-Plus (Stable Micro Systems). The compressive modulus is calculated on the basis of strain change from 0 to 5%. Shear strain measurements are performed with a Haake mars. Frequencies are applied at a fixed total shear stress (1 Pa) and 0.21N. Oscillation tests are performed to measure G' and G" after 3 weeks of gelation.

Preferably, the hydrogel and hydrogen solution comprising silylated biomolecules used in the different aspects of the invention are able to form a self-reticulating hydrogel at a pH between 7 and 12.

As used herein, the terms «hydrogel» and «hydrogel solution» which are used indifferently mean a network of polymer chains that are water-insoluble, in which water is the dispersion medium.

As used herein, the term "silylated biomolecules" means any organic or synthetic molecules onto which are grafted a silyl function, preferably an alkoxysylane. Silylation allows the formation of covalent bonds between the biomolecules constituting the hydrogel as a function of pH. The silylated biomolecules are thus able to form a pH-dependent self-reticulating hydrogel.

The term "organic molecule" is intended to mean any molecule that is produced by a living organism or that is a derivative thereof, including large polymeric molecules such as proteins, polysaccharides, and nucleic acids as well as small molecules such as primary metabolites, secondary metabolites, and natural products.

The term "synthetic molecule" is intended to mean any molecule that is produced by chemical methods, such as proteins, polysaccharides, nucleic acids and a mix thereof.

As examples of biomolecules, mention may be made of:
 lipid derivatives such as phospholipids, glycolipids and sterols,
 chemical messengers such as hormones and neurotransmitters,
 vitamins,
 sugar derivatives such as carbohydrate, disaccharide, oligosaccharides, polysaccharides (including cellulose),
 amino acid derivatives such as amino acids (natural and/or non-standard), peptides, oligopeptides, polypeptides, proteins (said peptides, oligopeptides, polypeptides and proteins containing natural and/or non-standard aminoacid),
 nucleotides derivatives such as nucleotides, and biological polymers such as deoxyribonucleic acid (DNA), ribonucleic acid (RNA),
 biopolymers such as lignin, proteins, DNA, RNA, oligosaccharides, polysaccharides.

Preferably, the biomolecule is a polysaccharide, a protein, or a peptide.

As used herein, the term "polysaccharide" means a polymer made up of many monosaccharides joined together by glycosidic bonds. Natural and synthetic polysaccharides are included. Examples of polysaccharide are cellulose and derives thereof, for instance hydroxypropylmethylcellulose (HPMC), hydroxyethylcellulose (HEC), and carboxymethylcellulose (CMC), pectin, chitosan and hyaluronic acid.

As used herein, the term "protein" means a polymer made of amino acids arranged in a linear chain and joined together by peptide bonds between the carboxyl and amino groups of adjacent amino acid residues. Glycoprotein as well as proteins containing natural and/or non-standard aminoacid are included. Albumin, laminin, gelatin, fibronectin, vitronectin and collagen are examples of protein.

The hydrogel may contain either only one kind of silylated biomolecule (i.e. all the biomolecules forming the polymer are the same), or silylated biomolecules of different nature, preferably two different silylated biomolecules, more preferably one silylated polysaccharide and one silylated protein or peptide.

In a preferred embodiment, the hydrogel contains a silylated HPMC, a silylated HEC or a silylated CMC polymer.

In a particularly preferred embodiment, the hydrogel contains only silylated HPMC.

In another preferred embodiment, the hydrogel is formed with:
- silylated collagen and silylated HPMC (leading to a hydrogel containing HPMC and collagen),
- silylated hyaluronic acid and silylated HPMC (leading to a hydrogel containing HPMC and hyaluronic acid),
- silylated tetrapeptide Arg-Gly-Asp-Ser (hereafter abbreviated "RGDS") and silylated HPMC (leading to a hydrogel containing HPMC and RGDS), or
- silylated pectin and silylated hyaluronic acid (leading to a hydrogel containing pectin and hyaluronic acid).

The silylated biomolecules used to carry out the invention are preferably stable in aqueous solution at a pH greater than or equal to approximately 12.4.

Thus, the aqueous solution comprising silylated biomolecules of the invention are preferably liquid at a pH of about 12.4 or above.

As used herein, the expression "aqueous solution" means a solution wherein water is the major solvent.

Acidification of the solution causes a gradual increase in viscosity, due to the condensation of the silylated biomolecules via the formation of —Si—O—Si— covalent bond, and the formation of hydrogel. Because highly basic pH is detrimental for cells, even when cells are exposed to it for a short period, the silylated biomolecules is contacted with an acid in an aqueous solution to obtain a final aqueous solution at physiological pH (i.e. with a pH value from 7.2 to 7.6, preferably 7.4), before cardiomyocytes or stem cells are added. The hydrogels and the aqueous solution comprising silylated biomolecules of the invention are preferably capable of gelation at physiological pH.

Addition of cells must occur before the total gelation of the final solution to hydrogel, preferably from a few seconds to 15 minutes after having contacted the silylated biomolecules with an acid and having obtained a final aqueous solution of pH from 7.2 to 7.6.

Processes for preparing silylated biomolecules and hydrogels according to the invention are well known by one skilled in the art. For instance, processes for the preparation of silylated HPMC and silylated HEC and for the preparation of hydrogel therefrom are described in US application 2007/0212389.

Methods for preparing silylated biomolecules are also described in application PCT/EP2011/050981. PCT/EP2011/050981 also disclosed the preparation of hydrogel comprising two different kinds of silylated biomolecules, in particular a silylated polysaccharide and a silylated protein or peptide.

Depending on whether the biomolecule used as starting material is carrying an amine or an alcohol function, or a carboxylic acid function, the two processes described below (and disclosed in application PCT/EP2011/050981) may be used to prepare silylated biomolecules.

For preparing a silylated biomolecule using a biomolecule carrying an alcohol or amine function, preferably chosen from a peptide, an oligopeptide, a protein, a deoxyribonucleic acid, a ribonucleic acid, pectin, chitosan, hyaluronic acid, a glycolipid as a starting material, the process (hereafter called "process 1") comprises a step of reacting said biomolecule with a silylation agent having the following formula (II) or (IIbis):

$$O=C=N-(CH_2)_m-Si(OR_1)(O)_p R_2 (O)_q R_3 \quad (II)$$

$$CH_2-CH-(CH_2)_m-Si(OR_1)(O)_p R_2 (O)_q R_3 \quad (IIbis)$$
         \O/ wherein:
m is an integer ranging from 1 to 6,
p and q are independently 0 or 1, and
$R_1$, $R_2$ and $R_3$ each independently represent a $C_1$-$C_6$ alkyl group.

Silylated biomolecules of formula (I):

$$A-X-(CH_2)_m-Si(OR_1)(O)_p R_2 (O)_q R_3 \quad (I)$$

wherein:
A is a biomolecule chosen from a peptide, an oligopeptide, a protein, a deoxyribonucleic acid, a ribonucleic acid, pectin, chitosan, hyaluronic acid, a glycolipid, and a polysaccharide
m is an integer ranging from 1 to 6,
p and q are independently 0 or 1,
X is a —NHCONH— or a —OCONH— moiety, and
$R_1$, $R_2$ and $R_3$ each independently represent a $C_1$-$C_6$ alkyl group. are obtained by process 1.

During the process, the amine or the alcohol function of the biomolecule reacts with the isocyanate function of the silylation agent of formula (II), leading to the formation of an urea bond (—NHCONH—) (if the biomolecule is carrying an amine function) or a carbamate bond (—OCONH—) (if the biomolecule is carrying an alcohol function) according to the following scheme:

$$A-NH_2 + O=C=N-(CH_2)_m-Si(OR_1)(O)_p R_2 (O)_q R_3 \longrightarrow$$

$$A-N(H)-C(=O)-N(H)-(CH_2)_m-Si(OR_1)(O)_p R_2 (O)_q R_3 \quad (Ia)$$

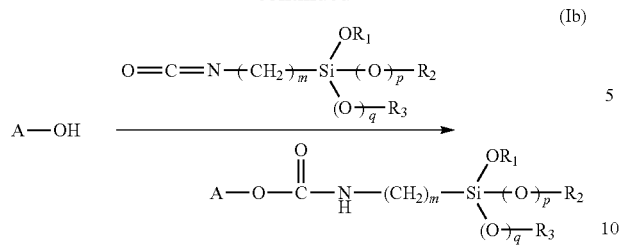

In one embodiment of process 1, the biomolecule is carrying an alcohol function and is preferably chosen from a deoxyribonucleic acid, a ribonucleic acid, pectin, chitosan, hyaluronic acid, a glycolipid and optionally from a peptide, an oligopeptide, a protein, when said peptide, oligopeptide, or protein comprise a moiety (an amino acid for example) carrying an alcohol function, for example the RGDS.

In one other embodiment of process 1, the biomolecule is carrying an amine function and is preferably chosen from a peptide, an oligopeptide, a protein, a deoxyribonucleic acid, a ribonucleic acid and chitosan. The biomolecule used in the process can also carry both an alcohol function and an amine function, for example when the biomolecule is chitosan.

In a preferred embodiment of process 1, the silylation agent used in the process is 3-isocyanatopropyltriethoxysilane.

Preferably, when the biomolecule is carrying amine functions, part of said amine functions are not protonated in the reaction medium. The lone pair of the amine has indeed to be available to attack the isocyanate function.

The temperature of the reaction of process 1 is not critical and may vary in wide range. The reaction is generally carried out at a temperature from −15° C. to 40° C., preferably 0° C. to 30° C., more preferably from 15° C. to 25° C., which is advantageous as no denaturation of biomolecule occurs. Preferably, process 1 is carried out under inert atmosphere, for example under argon or nitrogen.

The reaction time is usually lasts from one hour to one week, preferably from twelve hours to five days, more preferably from one to three days.

Process 1 is generally carried out in a solvent. There is no particular restriction on the nature of the solvent to be used, provided that it has no adverse effect on the reaction or on the reagents involved. Organic solvents or mixture of organic solvent with an aqueous solution, typically water, are preferred. Examples of suitable organic solvents include acetonitrile, acetone, dimethylformamide and dimethylsulfoxide.

In one embodiment, process 1 is carried out in an anhydrous solvent, such as anhydrous acetonitrile, anhydrous acetone, anhydrous dimethylformamide or anhydrous dimethylsulfoxide, and in the presence of a base, preferably an organic base, usually an organic base containing a nitrogen atom which can be protonated, for example triethylamine, pyridine or trimethylamine.

In one other embodiment, process 1 is carried out in a mixture comprising an aqueous solution and a solvent miscible in water, such as acetonitrile, acetone, dimethylformamide and dimethylsulfoxide. The mixture is preferably a mixture of water and of dimethylsulfoxide. No base is required for this embodiment.

For preparing a silylated biomolecule using as starting material a biomolecule carrying a carboxylic acid or a carboxylate function, a process is described therein (hereafter called "process 2"). This process for the preparation of a silylated biomolecule of formula (I) as defined above, comprising the steps consisting of:

a) reacting a biomolecule carrying a carboxylic acid or a carboxylate function, preferably chosen from a peptide, an oligopeptide, a protein, pectin, hyaluronic acid, with 1-ethyl-3-(3-dimethylaminopropyl)carbodiimide hydrochloride (EDC.HCl) or with 1,1'-carbonyldiimidazole (CDI), then b) adding to the reaction medium obtained in step a) a silylation agent having the following formula (III):

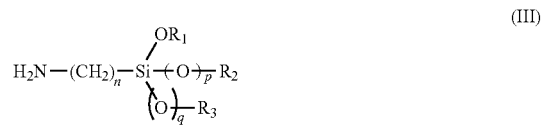

wherein, n is an integer ranging from 1 to 6 p and q are independently 0 or 1, and $R_1$, $R_2$ and $R_3$ each independently represent a $C_1$-$C_6$ alkyl group.

Silylated biomolecules of formula (I), wherein X is a —CONN— moiety, are obtained by process 2. During process 2, the carboxylic function of the biomolecule is activated with EDC.HCl in step a) and then reacts with the amine function of the silylation agent of formula (III), leading to the formation of an amide bond (—CONH—) according to the following scheme:

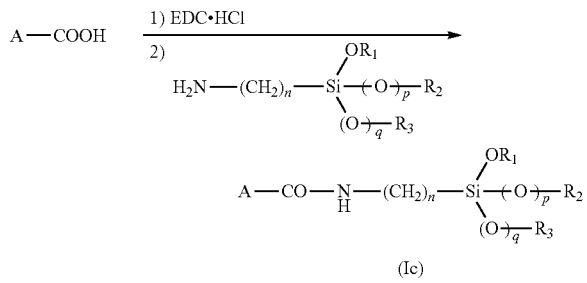

Preferred biomolecule used as starting material in step a) of process 2 are a peptide, an oligopeptide, a protein, pectin, and hyaluronic acid.

Step a) of process 2 can be carried out in the presence of a catalyst, such as N-hydroxysuccinimide.

The silylation agent used in step b) of process 2 is preferably (3-aminopropyl)triethoxysilane.

When EDC.HCl is used, steps a) and b) of process 2 are generally carried out in an aqueous solution, the pH of which is preferably from 4 to 6, most preferably from 4.7 to 5.3, preferably in water. When CDI is used, steps a) and b) of process 2 are generally carried out in dichloromethane or acetonitrile.

Steps a) and b) of process 2 are generally carried out at a temperature from −15° C. to 40° C., preferably 0° C. to 30° C., more preferably from 15° C. to 25° C., which is advantageous as no denaturation of biomolecule occurs.

Step a) of process 2 usually lasts from 4 h to 24 h, preferably from 12 h to 18 h, and step b) of process 2 usually lasts from 4 h to 24 h, preferably from 12 h to 18 h.

Both processes 1 and 2 lead to the formation of a strong covalent bond between the silylation agent and the biomolecule.

The weight concentration of the biomolecule used as starting material in the solvent in processes 1 and 2 is generally from 0.01 to 30%, preferably from 0.1 to 20%, more preferably from 0.5 to 15%.

Advantageously, processes 1 and 2 are carried out without any metal catalyst, more particularly tin based catalyst.

When process 2 wherein EDC. HCl is used is carried out, the reaction medium is generally homogeneous. When process 1 or process 2 wherein CDI is used are carried out, the reaction medium is generally heterogeneous. A suspension of the biomolecule in the solvent is generally observed, which can be isolated easily from the reaction mixture, for example by sedimentation or centrifugation.

The cardiomyocytes and the stem cells which are able to differentiate into cardiomyocytes used in the different aspects of the invention may be, for example, human, non human primate, rat, dog, mouse, or cat cells, more preferably human cells.

The stem cells may be, for example, embryonic stem cells, or adult stem cells such as skeletal myoblasts (stem cells from muscle), bone-marrow-derived stem cells (in particular mesenchymal stem cells), adipose-derived mesemchymal stem cells, cardiac stem cells (disclosed by Beltrami et al., Cell, 114: 763-776, 2003).

In a preferred embodiment, stem cells are mesenchymal stem cells, more preferably bone-marrow-derived mesenchymal stem cells.

Methods for isolating embryonic and adult stem cells are well known by the person skilled in the art, and are for example disclosed in Pittenger et al. (Circ Res., 95(1): 9-20, 2004, PMID: 15242981), and in Blin et al. (J. Clin. Invest., 1; 120(4):1125-39, 2010 doi: 10.1172/JCI40120. Epub 2010 Mar. 24. PMID 20335662).

The stem cells may also be induced pluripotent stem cells (hereafter abbreviated "iPS"), that is population of cells with characteristics reminiscent of embryonic stem cells which is generated from somatic tissues through nuclear reprogramming via the ectopic expression of genes related to pluripotency. Processes for generating iPS cells are for instance described by Takahashi et al. (Cell, 131: 861-872, 2007), Yu et al. (Science, 318: 1917-1920, 2007) and Okita et al. (Nature, 448: 313-317, 2007).

In embodiments of the different aspects of the invention where cardiomyocytes are used, said cardiomyocytes may be derived from stem cells or iPS cells.

Further, in embodiments of the different aspects of the invention where stem cells able to differentiate into cardiomyocytes are used, the hydrogel may comprise agents which allow induction of cardiomyocyte differentiation, so that the final cells obtained are cardiomyocytes. Examples of agents used in protocols of cardiac differentiation of stem cells are disclosed by Blin, et al. (Curr. Stem Cell Res. Ther., 5(3): 215-26, 2010). Preferably, where stem cells able to differentiate into cardiomyocytes are mesemchymal stem cells, in particular adipose-derived mesemchymal stem cells, the hydrogel does comprise agents which allow induction of cardiomyocyte differentiation.

Buffering solutions which may be used to produce a final aqueous solution with a physiological pH are well known to one of ordinary skill in the art. Examples of such a buffering solution are 4-(2-hydroxyethyl)-1-piperazineethanesulfonic acid (HEPES, HCl).

The present invention will be further illustrated by the additional description and drawings which follow, which refer to examples illustrating the characterization of the properties of a hydrogel according to the invention comprising cardiomyocytes or stem cells, and its use to preserve cardiac function and left ventricular remodeling in acute stage following myocardial infarction. It should be understood however that these examples are given only by way of illustration of the invention and do not constitute in anyway a limitation thereof.

Cardiomyocytes were cultured in 2D with or without Si-HPMC (control) or in the presence of actinomycin-D (5 µg/ml) during the indicated times. Viability was assessed by MTS activity. Results are expressed as relative MTS activity compared with the respective control. *$P<0.001$ as compared to control conditions.

Figure 2:
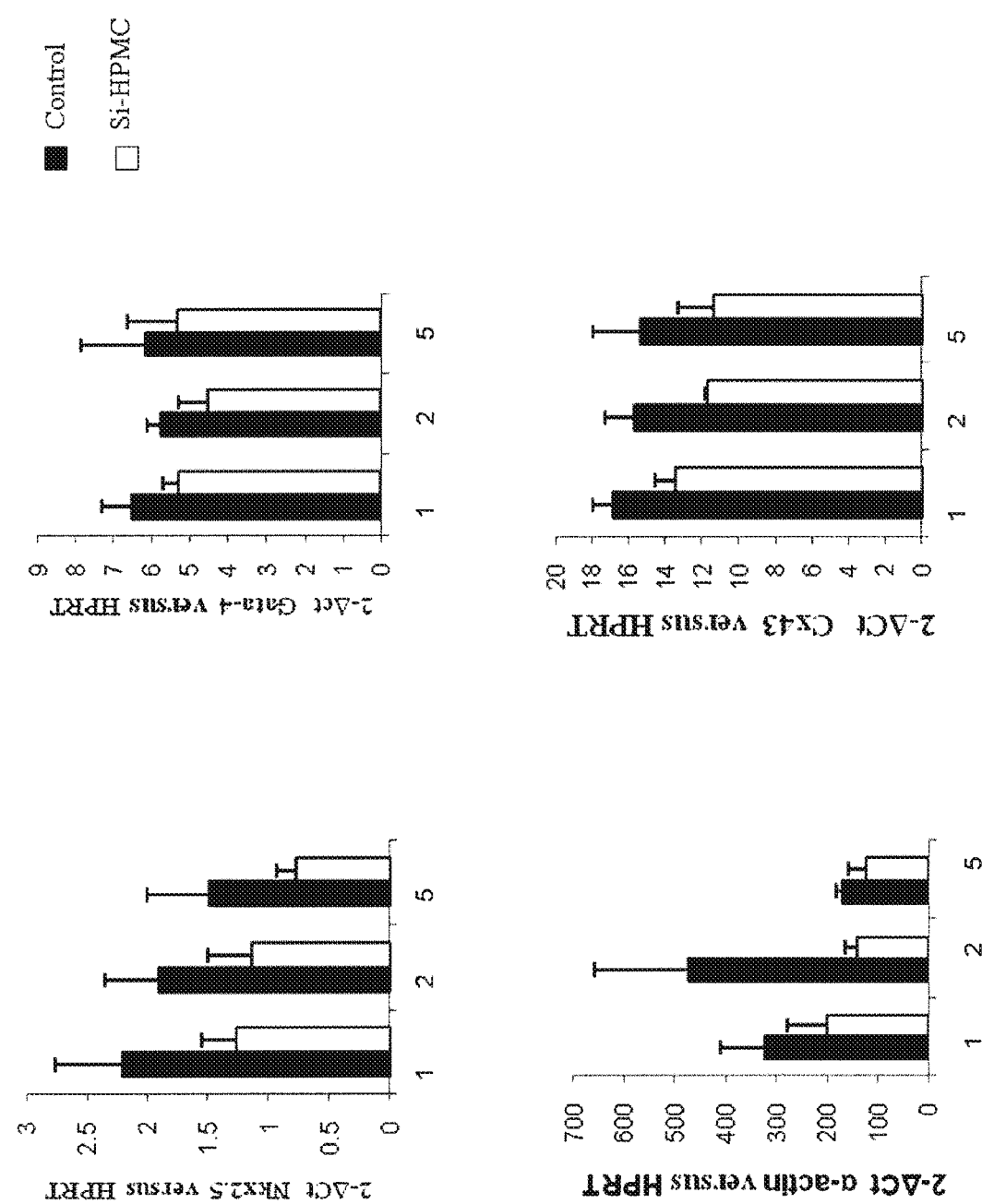

FIG. 2 illustrates a real-time RT-PCR analysis of cardiomyocyte phenotype in culture in 2D with the Si-HPMC hydrogel. mRNA was harvested from cardiomyocytes after 1, 2 and 3 days of culture with or without Si-HPMC (control). Real-time RT-PCR was performed by using nkx2.5, gata4, cardiac sarcomeric α-actin and connexin43 and corrected by HPRT gene expression levels. *$P<0.001$.

Figure 3:
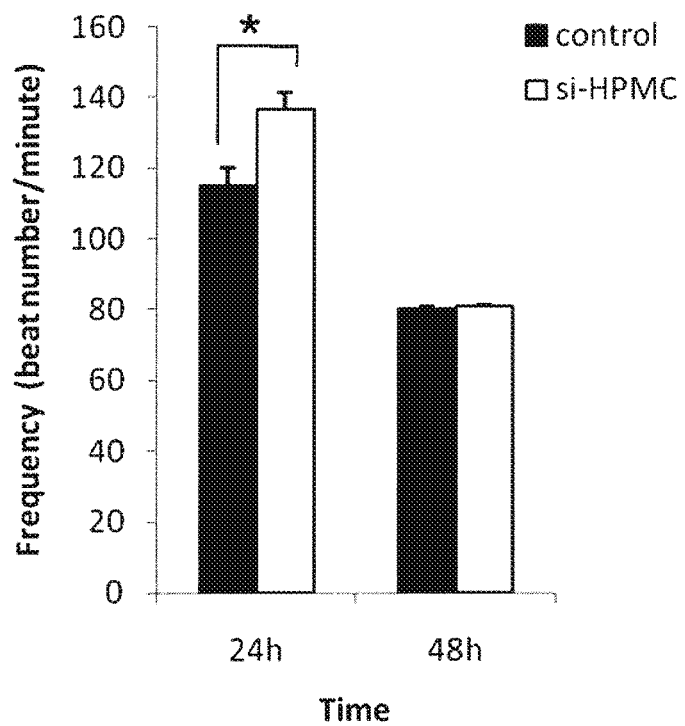

FIG. 3 illustrates the quantification of cardiomyocyte contractility in 2D culture. The contractility was quantified manually by counting the cardiomyocytes beats for one minute. This frequency was measured after 24 and 48 hours of culture in 2D of cardiomyocytes with or without (control) Si-HPMC. Results are expressed as beat number/minute. *$P<0.01$.

Figure 4:
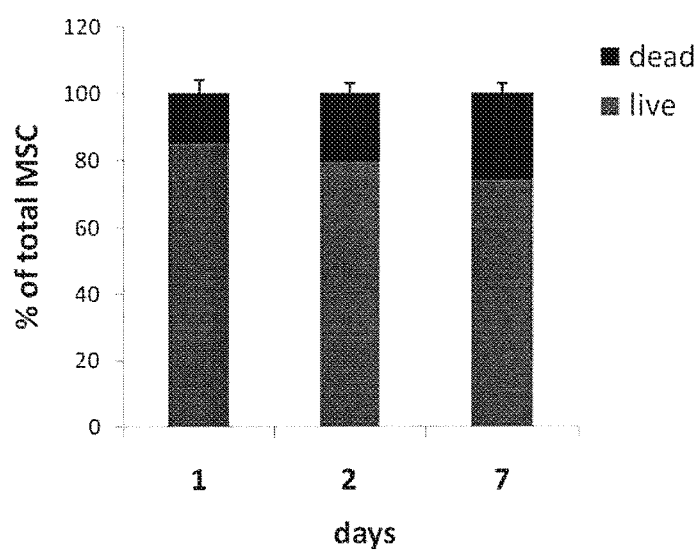

FIG. 4 illustrates the three-dimensional cellular viability of MSCs in Si-HPMC hydrogel. MSCs were cultured in 3D into Si-HPMC hydrogel during the indicated times. Cells were stained with calcein-AM and EthD-1, which label living cells in green and dead cells in red, respectively. MSC viability was assessed by the intensity of green fluorescence, as a consequence of incorporation of the calcein fluorescent probe into cell cytoplasm. Percentages of living and dead MSCs cultured in 3D within hydrogel over 7 days (p=NS as compared between groups).

Figure 5:
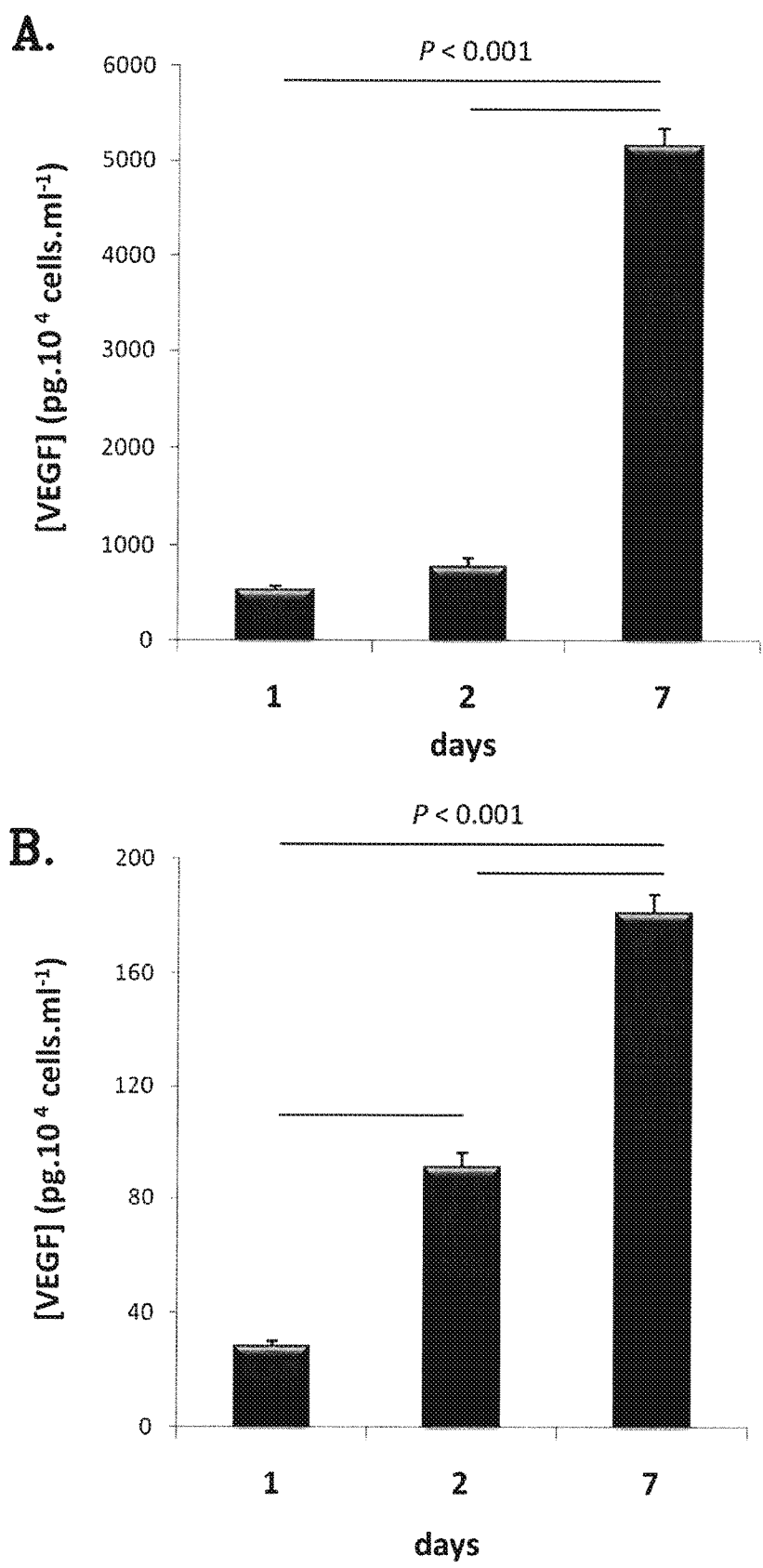

FIG. 5 illustrates measurements of VEGF protein concentrations by ELISA assay. VEGF concentrations in (A) control supernatants of MSCs cultured without hydrogel ($p<0.001$ for all comparisons) and in (B) supernatants of MSCs cultured in 3D within hydrogel ($p<0.001$, for all comparisons). VEGF concentrations were expressed as pg·ml$^{-1}$ for $10^4$ cells.

Figure 6:
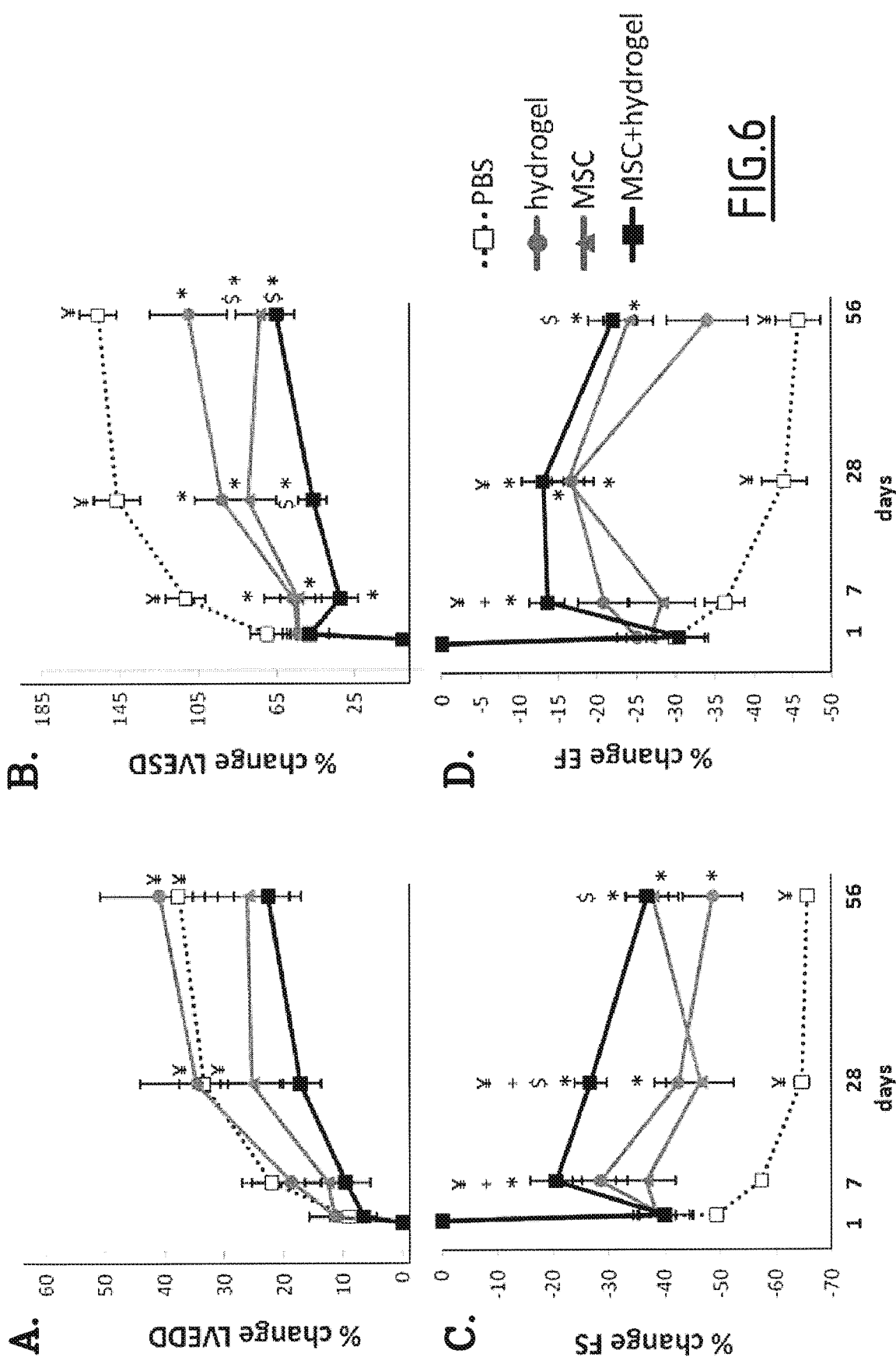

FIG. 6 illustrates the evaluation of cardiac function by echocardiography in rats after myocardial infarction (MI). Measurements were performed at baseline before MI and 1, 7, 28 and 56 days after MI. (A) LV end-diastolic diameter (LVEDD), (B) LV end-systolic diameter (LVESD). (C) The fraction shorting (FS) and (D) Ejection fraction (EF). ¥$p<0.05$ compared to day 1 post-infarction in the same group, *$p<0.001$ compared to the PBS group at the same time-point, $p<0.05$ compared to the Hydrogel group at the same time-point and +$p<0.05$ compared to the MSCs at the same time-point.

Figure 7:
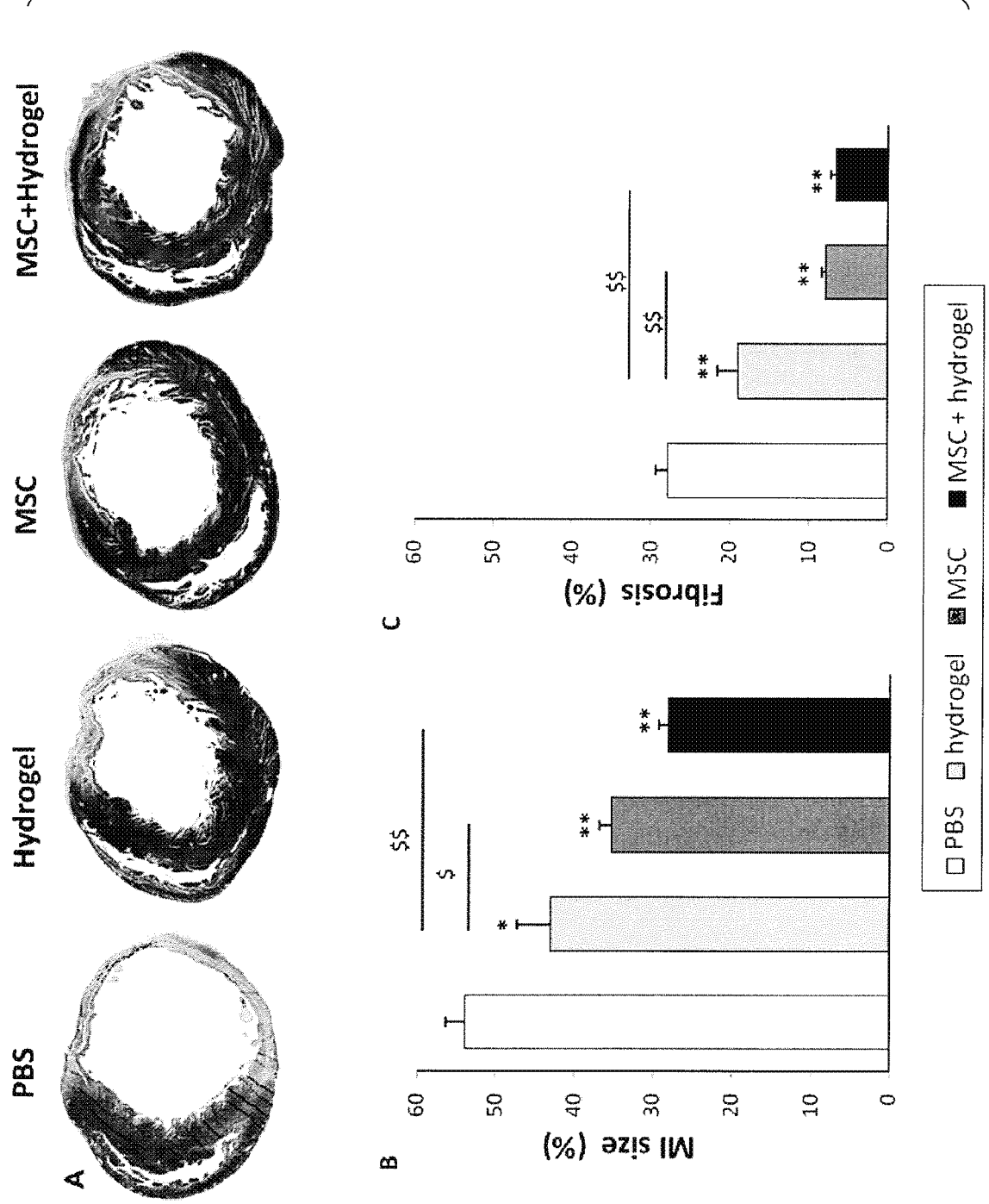

FIG. 7 illustrates the effects on Myocardial Infarction and fibrosis of injection of PBS (control group), Hydrogel, MSC, or MSC+hydrogel into myocardium of rats suffering from myocardial infarction. (A) Representative histologic sections of Masson trichrome staining for infarct size measurement (collagen-rich areas in blue and healthy myocardium in red; original magnifications: ×40). (B) Circumferential infarct size (MI size) to total LV tissue and (C) percentage of fibrosis to LV tissue. For (B) and (C): *$p<0.05$ and

**p<0.001 compared to the PBS group and $p<0.05 and $$p<0.001 compared to Hydrogel group.

Figure 8:
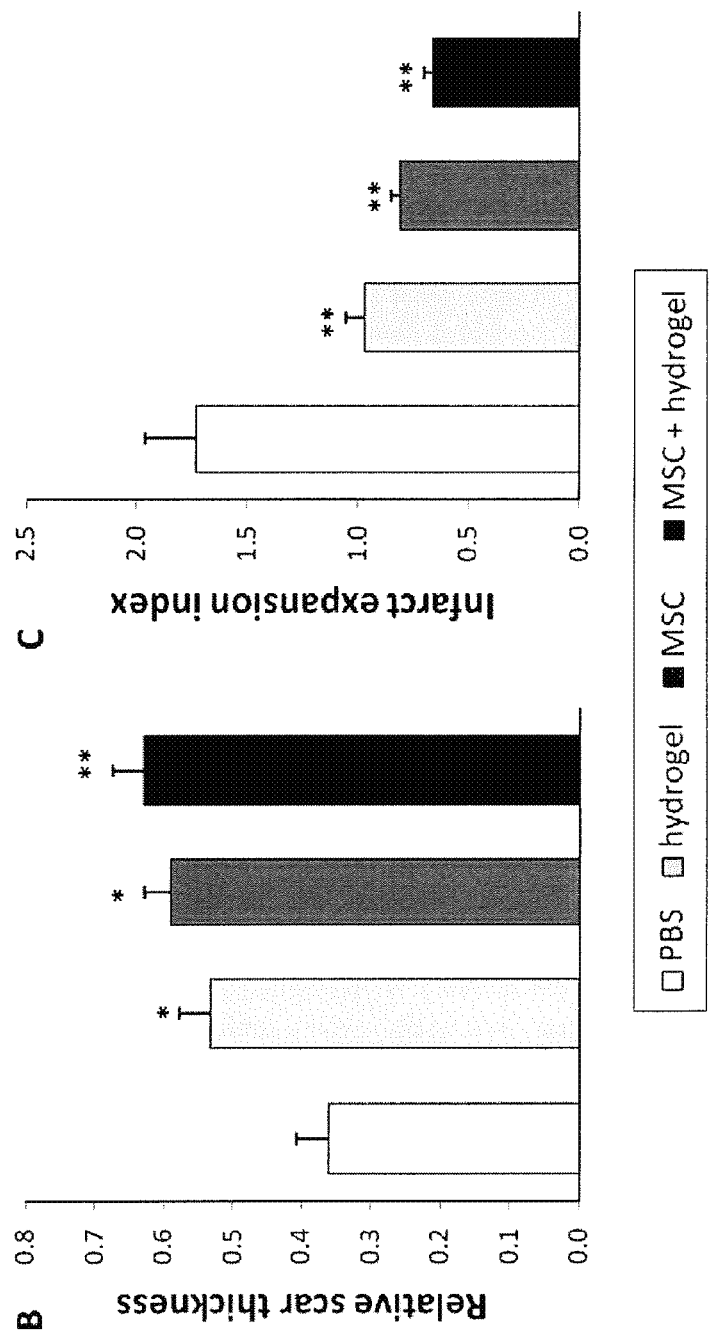

FIG. 8 illustrates the effects on scar thickness and infarct expansion of injection of PBS (control group), Hydrogel, MSC, or MSC+hydrogel into myocardium of rats suffering from myocardial infarction. (A) Representative photomicrographs of Masson trichrome staining of the scar area (collagen-rich areas in blue and healthy myocardium in red; Original magnifications: ×100). (B) Relative scar thickness (average scar thickness/average wall thickness). (*p<0.05 and **p<0.001, two-way ANOVA). (C) Infarct expansion index ([LV cavity area/whole LV area]/relative scar thickness). For (B) and (C): *p<0.05 and **p<0.001.

EXAMPLES

Example 1

Preparation of Hydrogel

Materials
HPMC E4M TM (Colorcon—Dow Chemical, France)
Glycidoxypropyltriméthoxysilane (GPTMS) (Acros, Belgium)
HEPES and HCl (Sigma-Aldrich, St Louis, the USA)
NaOH and NaCl (International VWR, Fontenay-under-Wood, France)
Synthesis of Si-HPMC Hydrogel As previously described (Bourges et al., Adv. Colloid Interface Sci., 99: 215-228, 2002), the synthesis of Si-HPMC was performed by grafting 14, 24% of 3-GPTMS on E4M® in heterogeneous medium. Aqueous solution of Si-HPMC was prepared at 3% w/w concentration. The powder was dissolved in sodium hydroxide solution (0.2M NaOH) at 25° C. for 48 h. Si-HPMC solution was then dialyzed in a dialysis bag against 3.8l of NaOH solution (0.09M) for 12 h and with 4 of NaOH solution (0.09M) for 2 h. The solution was then sterilized by steam (121° C., 30 mn). To allow the formation of a reticulated hydrogel, 1 volume of the solution was finally mixed with 1 volume of a 0.13 M HEPES buffer.

Rheological Measurements

Dynamic rheological measurements were performed on a Haake Rheometer (rheostress 300) using a coni-cylindrical geometry with a diameter of 60 mm and a cone angle of 1°. We used a multiwave procedure with 3 frequencies 1, 3.2 and 10 Hz, and the imposed stress was 1 Pa. Oscillation tests measuring storage modulus (G') and loss modulus (G") were performed to study the self-setting process and gel point. Compressive modulus of scaffold was measured using a TA HD-Plus (Stable Micro Systems). Six specimens were tested after three weeks of reticulation and the compressive modulus was calculated on the basis of strain change from 0 to 5%. Shear strain measurements were performed with a Haake mars. Frequencies were applied at a fixed total shear stress (1 Pa) and 0.21N. Oscillation tests were performed to measure G' and G" after 3 weeks of gelation. Nine specimens were tested.

Results:

Rheological properties of Si-HPMC hydrogel mixed with one volume of a 0.13M buffer (1v1) were measured. The compressive modulus at 5% stress and the storage modulus (G') and loss modulus (G") of Si-HPMC were performed after three weeks of reticulation.

The final product (Si-HPMC) consisted of a reticulated hydrogel after 27.2±3.4 min with a pH value of 7.4. Dynamic rheological measurements were performed to characterize this hydrogel. Shear strain measurements were performed to determine de storage modulus (G'), which characterized the hard component and the loss modulus (G"), which characterized the liquid component. The compressive modulus reflects the capacity of a material to resist to strengths. When the limit of the compressive strength is reached, the hydrogel is destroyed. In the case of our Si-HPMC hydrogel, compressive modulus was about 328.56±96.97 Pa. After three weeks of reticulation and a finished self-setting process, we observed a value of 343.17±106.5 Pa for the storage modulus (G') and a value of 44.48±15.43 the loss modulus (G").

Example 2

Preparation and Cell Culture

Materials
Dulbecco'S modified Eagle medium (DMEM), alpha Modified Eagle medium (α-MEM)
Hank's Balanced sodium salt (HBSS), horse serum, Penicillin/streptomycine, L-glutamine, collagenase II (284.00 unit/mg), Trypsine/EDTA (Invitrogen corporation, Paisley, the U.K.)
pancreatin (0.1 mg/ml), laminin (Sigma-Aldrich, St-Louis, USA)
Fetal Calf Serum (FCS) (Hyclone Perbio, Thermo Fisher scientific)
Animals: neonatal C57Bl/6j mice and Lewis female rats (Janvier, France)

Isolation and Culture Cardiomyocytes:

Primary cardiomyocytes were isolated from 1 or 2-day-old neonatal C57Bl/6j mice hearts. Briefly, neonatal mice were sacrificed and hearts were rapidly removed and placed into dishes on ice. After atria and great vessels were removed, hearts were minced and digested repeatedly (10 min×8) in HBSS solution supplemented with collagenase II (284.00 unit/mg) and pancreatin (0.1 mg/ml) at 37° C. and 5% CO2. After centrifugation, cells were resuspended in culture media (DMEM with 10% horse serum, 5% SVF, 1% penicilline/streptomycine).

For two dimensional culture with the Si-HPMC hydrogel, cardiomyocytes were plated in 24-well plates (coated with laminin 10 μg/ml) at the density of 55 000 cells/cm$^2$ and maintained at 37° C. in a humidified atmosphere and 5% CO2. After 48 hr, culture medium was removed and 500 μl of Si-HPMC were added in each well. Samples were incubated at 37° C. for 1 h before adding 500 μl of culture medium. For 3D-culture of suspended cardiomyocytes in Si-HPMC hydrogel, 10 μl of culture medium containing 9×10$^6$ cardiomyocytes were mixed with 1 ml of Si-HPMC. 500 μl of cells/Si-HPMC mixture were seeded in 12-well plates and incubated at 37° C. and 5% CO2. After 1 hr incubation, 1 ml of culture medium was added in each well and plates were incubated. For cardiomyocyte 3D-culture in a micro-drop of Si-HPMC hydrogel, 5 μl of culture medium containing 2×10$^4$ cardiomyocytes were directly injected in a micro-drop of Si-HPMC after 2 hours of polymerization.

Isolation and Culture of MSC:

Bone marrow (BM) was obtained from Lewis female rats weighing 180-200 g. BM from femurs cavity was flushed with α-MEM medium containing 10% FBS and 1% penicillin/streptomycin, and the cell suspension was centrifuged (1200 rpm, 7 min). Cells were then plated in culture flasks (200 000 cells/cm2). Non adherent cells were removed after 72 hours, and MSCs were recovered by their capacity to strongly adhere to plastic culture dishes. MSCs were then routinely cultured and were used for experiments after the third passage.

Example 3

Study of the Cytotoxicity of Hydrogel

Materials
Plate culture 24 wells Corning-Costar (Corning BV, Schiphol-Rijk, The Netherlands).
Actinomycin D and Dyméthylsulfoxyde (DMSO) (Sigma-Aldrich)
Methyl Tetrazolium Salt (MTS) (Titer Concealment 96 MTS, Promega corporation, Madison, Wis.).
Buffered salt phosphates (PBS, Invitrogen corporation).

A. Cardiomyocyte Viability:

Cardiomyocyte viability in 2D culture was measured using an MTS assay as previously described (Relic et al., 2001; Magne et al., 2003). As a control, cells were also cultured in the absence of Si-HPMC or in the presence of actinomycin-D (5 mg/ml), an inhibitor of RNA polymerase (Kimura et al., 2002) used as a potent inducer of cell death. After 24 and 48 hours, hydrogels and culture media were removed and MTS solution was added in each well for 1-3 h according to the manufacturer's instructions. Finally, colorimetric measurement was performed on a spectrophotometer at an optical density of 490 nm. Results were expressed as relative MTS activity compared to control condition (cells cultured in the absence of Si-HPMC).

Figure 1:
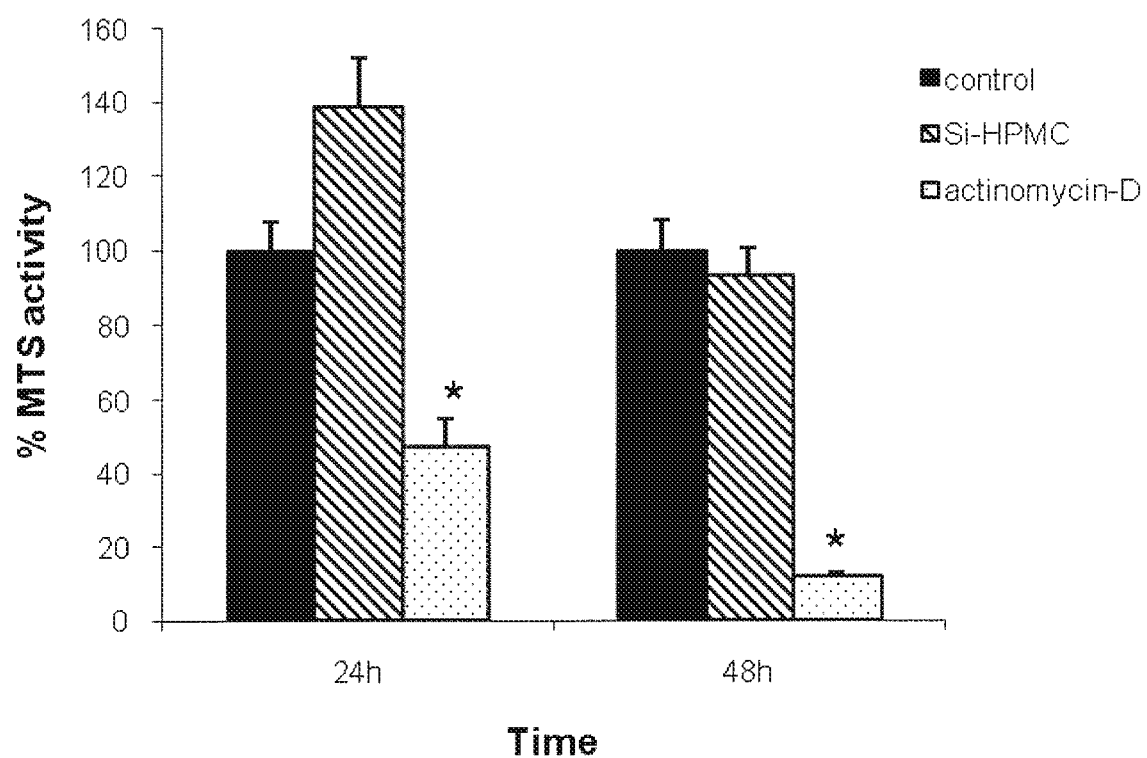
FIG. 1 illustrates viability of cardiomyocytes cultured with or without Si-HPMC.

Results:

Cardiomyocyte viability was evaluated using MTS activity at 24 and 48 hours of 2D culture in presence of Si-HPMC hydrogel. No significant difference was observed between control cultures and the cultures carried out in contact with hydrogel (see FIG. 1). On the other hand, the actinomycin-D, inhibitor of the transcription, used here as cytotoxicity positive control induced a significant reduction in MTS activity of cardiomyocytes after 24 hours of culture. In the presence of actinomycin D MTS activity decreased by nearly 55% after a 24 h treatment and by 90% after a 48 h treatment. Therefore, the Si-HPMC hydrogel maintains cardiomyocyte viability.

B. Cardiomyocyte Phenotype

Transcripts Analyses:
Materials:
RNeasy Mini Kit (Qiagen S.A., France)
High-capacity cDNA Archive kit (Applied Biosystems, life technologies corporation, USA)
Taqman gene expression (Applied Biosystems, life technologies corporation, USA)

In order to analyze cardiomyocyte phenotype, expression of mRNA coding for cardiomyocyte markers was quantified by RT-PCR. RT-PCR analysis of transcripts was performed on cardiomyocytes in 2D culture in the absence or presence of Si-HPMC.

Total RNA extraction and DNAse treatment Total RNAs from each cardiac sample were isolated and DNase-treated with the RNeasy Fibrous Tissue Mini Kit following manufacturer's instructions.

Reverse transcription: First-stand cDNA was synthesized from 200 ng of total RNAs using the High-capacity cDNA Archive kit.

Reaction of polymerase in chain (PCR) On-line PCR was performed using the following primers: nkx2.5 (nkx2.5, Mm00657783_m1), gata4 (gata4, Mm00484689_m1), actin alpha cardiac muscle 1 (actc1, Mm01333821_m1), gap junction protein alpha 1 (gja1, Mm00439105_m1). Fluorescence signals were normalized to the hypoxanthine guanine phosphoribos yl transferase 1 (hprt1, Mm03024075_m1), used as reference gene. Data were averaged and then used for the $2^{-\Delta CT}$ calculation. $2^{-\Delta CT}$ corresponded to the ratio of each gene expression versus hprt.

Results:

The ability of Si-HPMC to maintain cardiomyocyte phenotype after 1 day, 2 and 5 days of 2D culture was evaluated by relative quantification of cardiogenic marker (nkx2.5, gata-4, cardiac sarcomeric α-actin and connexin 43) mRNAs, using TaqMan real-time PCR (see FIG. 2). Expression levels of these cardiomyocyte markers were maintained during the 5 days of culture in presence or absence d'HPMC. Importantly, the presence of the Si-HPMC hydrogel did not alter expression levels of these genes in cardiomyocytes.

Immunostaining:
Materials:
Formaldehyde solution 37% (Sigma-Aldrich)
Triton X-100 (Sigma-Aldrich)
Bovine serum albumin (Sigma-Aldrich)
  Polyclonal antibodies: anti-nkx2.5 and anti-gata4 (Santa Cruz Biotechnology, USA).
Monoclonal anti-connexin 43(Millipore)
Secondary antibodies Alexa fluor (Molecular Probes, Leiden, The Netherlands)
Vectaschield® medium with DAPI nuclear (vector laboratories, US. Headquaters).

Cardiomyocytes were fixed in 4% formaldehyde for 30 min at room temperature and permeabilized with 0.2% Triton X-100, bovine serum albumin, and phosphate-buffered saline (BSA-PBS). then, cells were incubated for 1 h at room temperature with primary antibodies: polyclonal anti-nkx2.5 (1:500), polyclonal anti-gata4 (1:500), monoclonal anti-connexin 43 (1:100) and monoclonal anti-sarcomeric alpha actin (1:1000). Cells were washed and incubated for 45 min at room temperature with fluorescence-conjugated secondary antibodies at a 1:1000 dilution: Alexa fluor 568 mouse anti goat IgG, Alexa Fluor 488 goat anti-mouse IgG and Alexa fluor 594 goat anti-mouse IgG. Cells were washed carefully with PBS and the samples were mounted with Vectaschield® medium with DAPI nuclear. Cardiomyocytes were observed using fluorescence microscopy, and pictures were taken using a Zeiss Axioskop2 with equal exposure times. The extent of fluorescence was measured by using MetaMorpho microscope image analysis software (version 6.3).

Results:

The expression and localization of proteins nkx2.5, gata4, cardiac sarcomeric α-actin and connexin 43 were observed by immunofluorescence staining after 48 hours of culture (data not shown). The expression of both transcription factors nkx2.5 and gata-4 were maintained in the nuclei of cardiomyocytes cultured with Si-HPMC, as well as membrane expression of connexin 43. Staining for sarcomeric α-actin revealed typical sarcomeric striations in cardiomyocytes cultured in presence or absence of Si-HPMC. These results suggest Si-HPMC hydrogel maintained cardiomyocyte phenotype.

C. Cardiomyocyte Contractility

After 24 and 48 hours of culture in the presence or absence Si-HPMC, cardiomyocytes were observed by videoscopy using a Nikon eclipse TE200E microscope. Spontaneous contractions were quantified over one minute. Functional activity of 3D cultured cardiomyocytes was visualized using videoscopy after 48 hours of culture.

Results:

Cardiomyocyte contractility was qualitatively and quantitatively characterized by image analysis of the contraction videos. After 24 hours of 2D culture, cardiomyocytes began to display spontaneous contractions and after 48 hours their contractile activity was synchronous. Contraction rate was almost similar when cardiomyocytes were cultured in the absence or presence of the Si-HPMC hydrogel (see FIG. 3) (140 beats/min at 24 hrs and 80 beats/min at 48 hrs). The seeded cardiomyocytes suspended in Si-HPMC hydrogel showed a round morphology since these cells could not adhere to matrix. In addition, cells had very few intercellular contacts which prevented evaluation of electromechanical coupling. However after 48 hours of culture, several cardiomyocytes showed spontaneous contractile activity, cells had migrated and created contacts with neighboring cells favoring contraction. To promote electromechanical coupling between cells, cardiomyocytes were seeded into micro-droplets in the hydrogel. After 48 hours of culture, clusters of cells with synchronous contractility were observed. These results suggest that Si-HPMC hydrogel allows maintenance of cardiomyocyte contractile activity in 2D and 3D culture.

Example 4

Injection of Si-HPMC Hydrogel with MSC in Myocardium

Materials and Methods
Isolation and Culture of BM-MSC

Bone marrow (BM) was obtained from Lewis female rats weighing 180-200 g (Janvier France, http://www.janvier-europe.com). BM from femur cavity was flushed with α-MEM medium (Invitrogen corporation, Paisley, the U.K) containing 10% FCS (Hyclone Perbio, Thermo Fisher scientific), 1% L-Glutamin, 1% penicillin/streptomycin (Invitrogen) and 2 ng/ml of human FGF2 (AbCys P100-18B).The cell suspension was centrifuged (1200 rpm, 7 min). Cells were then plated in culture flasks (200 000 cells/cm2). Non adherent cells were removed after 72 hours, and mesenchymal stem cells (MSCs) were recovered by their capacity to strongly adhere to plastic culture dishes. MSCs were then routinely cultured and were used for experiments after verification of their phenotype by flow cytometric analysis for surface markers (CD29, CD45, CD90 and Sca1) at passage 3.

Silanized Hydroxypropyl Methylcellulose-based Hydrogel Preparation
Synthesis of Si-HPMC Hydrogel Hydroxypropyl methylcellulose (HPMC) E4M® was purchased from Colorcon-Down chemical (Bougival, France). The synthesis of Si-HPMC was performed by grafting 0.5% of silicium in weight on HPMC (E4M®) heterogeneous medium, as previously described by Boor P J, and Ferrans V J. (Am. J. Pathol., 121: 39-54, 1985) (Si-HPMC powder 3%) was solubilized in 0.2M NaOH under constant stirring for 48 h. The solution was dialyzed against 0.09 M NaOH using 6-8 kDa dialysis tubes (SpectraPor 1, Fisher Scientific, France). The resulting viscous solution (pH 12.6) and a 4-(2-hydroxyethyl)-1-piperazineethanesulfonic acid buffer (HEPES, pH 3.6; Sigma-Aldrich, St Louis, the USA) were separately steam sterilized by steam (121° C., 30 min) and then mixed using luer-lock syringes at a volume ratio of 1/1 as previously described by Bourges et al. (Adv. Colloid Interface Sci., 99: 215-228, 2002). Final product consists in hydrogel (pH=7.4) containing Si-HPMC concentration of 1.5%.

Rheological Measurements

Reticulation of 1 ml Si-HPMC was induced in 12-well plates. Dynamic rheological measurements were performed on a rotational rheometer (Rheostress 300, ThermoHaake®, Germany) using a coni-cylindrical geometry with a diameter of 60 mm and a cone angle of 1°. We used a multiwave procedure with 3 frequencies 1, 3.2 and 10 Htz, and the imposed stress was 1 Pa. Oscillation tests measuring storage modulus (G') and loss modulus (G") were performed to study the self-setting process and gel point. The gel points are given as the time taken for the liquid (G">G') to turn into a solid (G'>G"). They were determined according to a derived percolation theory (Fatimi et al., Acta Biomater., 5: 3423-3432, 2009). Compressive modulus of scaffold was measured using a TA HD-Plus (Stable Micro Systems). Six specimens were tested after three weeks of reticulation and the compressive modulus was calculated on the basis of strain change from 0 to 5%. Shear strain measurements were performed with a Haake mars. Frequencies were applied at a fixed total shear stress (1 Pa) and 0.21N. Oscillation tests were performed to measure G' and G" after 3 weeks of gelation. Nine specimens were tested.

Cytocompatibility of Si-HPMC Hydrogel
Cellular Viability in 3D Culture

For 3D culture, MSC viability was quantitatively assessed by Live & Dead assays (Kit, Invitrogen, France) along with confocal image analysis. Briefly, MSCs were dispersed into the hydrogels within the 5 minutes following their preparation at a final concentration of $1 \cdot 10^6$ cells/ml of hydrogel. 250 µl of mixture was molded into ultra-low attachment 24-well plates and incubated at 37° C. for 1 h to allow the hydrogels to crosslink. Afterwards, 500 µl of culture medium was added per well and the samples were incubated for 24 h, 48 h and 7 days before Live & Dead assays were performed. In each well, the culture medium was replaced by 200 µl of a solution containing 2.5 ml of culture medium supplemented with 0.25 µl of calcein-AM (5 mM) and 5 µL of ethidium homodimer-1(EthD-1; 2 mM).

After 5 to 10 minutes, the dye mixture was removed and the hydrogels were intensively rinsed with some phosphate buffered saline, before being observed on a confocal laser-scanning microscope Nikon A1R (Nikon France) equipped with an argon laser (488 nm) and a laser diode (561 nm).

Images were recorded in 512×512 pixels with an objective CFI Plan Fluor ELWD 40x×40 LD NA:0.6. Resonant mode was used in bidirectionnel scanning with average 16. For each sample, 6 random positions (x,y,z) were chosen within the hydrogel, and a stack of 100 planes were taken from these 6 positions along the z axis with 10 µm step size.

Images obtained per sample were analyzed and the percentages of living cells (in green) and dead cells (in red) were determined by using ImageJ (NIH) version 1.43u for Windows with the plugin "colour deconvolution". Each condition was tested in triplicate, and each experiment was repeated three times.

Secretion of VEGF of MSCs in 3D Culture

Secretion of vascular endothelium growth factor (VEGF) in supernatants from MSCs was quantified by specific enzyme-linked immunosorbent assay (ELISA) using a VEGF ELISA kit according to the manufacturer's protocol (R&D Systems, Minneapolis, Minn.). Briefly, MSCs were cultivated in 3 dimensional into Si-HMPC hydrogel ($10^6$ cells/ml of Si-HPMC hydrogel) and cell culture supernatant samples were collected from wells after 1, 2 and 7 days of culture. MSCs cultivated in 2 dimensions without hydrogel were used as control. Each condition was tested in triplicate, and each experiment was repeated three times.

Induction of MI in Rats and Implantation

Animal studies were performed in accordance with the regional Ethical Committee CREEA (Comités régionaux d'éthique en matière expérimentation animale). Female Lewis congenic rats (180-190 g) (Janvier France,) were anesthetized with a mix of isoflurane/oxygen inhalation (3%/97%), incubated and ventilated (Harvard Rodent Ventilator, Harvard Apparatus). A left lateral thoracotomy in the fourth intercostals space was performed to expose the anterior surface of the heart. The proximal left ascending coronary artery was identified and ligatured with a 6.0 polypropylene snare (Ethicon). The infarcted area was identified by the surface scar and wall motion akinesis. Immediately after coronary artery ligation, a total of 150 µl of Si-HPMC hydrogel alone (hydrogel), MSCs alone ($3.10^6$ cells) or in combination with the Si-HPMC hydrogel (MSC+hydrogel), or PBS (used as control), were delivered into the myocardium with a 26-gauge needle into 3 sites along the infarcted area. Sham-operated animals were subjected to the same surgical procedure without coronary artery ligation and injection. In all experiments, we at least 10 rats were used in each group.

Echocardioqraphic Measurements

Echocardiographic measurements were obtained at 1 day before MI (baseline), and 1 day and 7, 28 and 56 days after MI. Echocardiographic assessments were performed in-anesthetized rats (2% isoflurane inhalation) using a General Electric Vivid 7VR (GE Medical System; Milwaukee, Wis., http://www.gehealthcare.com) equipped with a 13-MHz transducer. Cardiac dimensions: Left ventricular end-diastolic diameter (LVEDD), end-systolic diameter (LVESD), and fraction shortening (LVFS) were recorded from M-mode images using averaged measurements from three to five consecutive cardiac cycles according to the American Society of Echocardiography. Left ventricular end-diastolic and end-systolic volumes (LVEDV and LVESV, respectively) were calculated from bidimensional long-axis parasternal views taken through the infarcted area by means of the single-plane area-length method ($V=(8 \times A^2)/(3 \times \pi \times L)$). LV ejection fraction (LVEF) was calculated as follows: $LVEF=((LVEDV-LVESV)/LVEDV) \times 100$. All measurements were averaged on three consecutive cardiac cycles and analyzed by a single observer who was blinded to the treatment status of the animals.

Histopathology

Rat hearts were harvested, washed in PBS (pH 7.4) and fixed in 10% formalin for histology. Hearts were embedded in paraffin and 6 µm sections were cut from the apex to the level just below ligation. Three evenly spaced sections were stained with Masson trichrome and observed with a Nikon TE2000-E inverted microscope.

Circumferential extent of scar to total LV tissue (Kanashiro-Takeuchi R M et al., Proc. Natl. Acad. Sci. USA., 107: 2604-2609, 2010), relative scar thickness, and infarct expansion index (Ruvinov et al., Biomaterials, 32: 565-578, 2011) were quantified using ImageJ (NIH) version 1.43u for Windows.

Average of epicardial and endocardial infarct ratios were calculated for each section based on measurement of epicardial and endocardial infarct lengths and epicardial and endocardial LV circumference. For each heart, infarct size was calculated as the average of the value obtained for the 3 analyzed sections. Relative scar thickness was calculated as average scar thickness divided by average wall thickness, averaged from 3 measurements of scar and septum thickness, respectively.average, Infarct expansion index was calculated as follows: [LV cavity area/whole LV area]/relative scar thickness. Percentage area of fibrosis in the remote left ventricle was quantified using an in-house image analysis program base on the following formula: % fibrosis=fibrotic area/(fibrotic area+healthy area).

Statistical Analysis

All values are shown as mean±SEM. Comparative studies of means were performed by using one-way ANOVA followed by post-hoc test when appropriate (Fisher's projected least significant difference) with $p<0.05$ as threshold for statistical significance. Echocardiographic parameters during 8-week follow-up were compared within groups and between groups using one-way ANOVA for repeated measurements followed by post hoc tests, respectively. For a given parameter, $p<0.05$ was considered significant. All tests were carried out using SigmaStat for Windows 3.5.

Results

Rheological Characteristics of Si-HPMC Hydrogel

Rheological properties of Si-HPMC solution mixed with acid buffer (1/1) were measured. The compressive modulus at 5% stress and the storage modulus (G') and loss modulus (G") of Si-HPMC were performed after three weeks of reticulation. The final product (Si-HPMC) consisted of a reticulated hydrogel with a pH value of 7.4 after 27.2±3.4 min. Dynamic rheological measurements were performed to characterize this hydrogel including shear strain measurements to evaluate the storage modulus (G'), which characterizes the hard component, and the loss modulus (G"), which characterizes the liquid component. Compressive modulus, which reflects the stiffness of the material in compressive experiment, was 328.6±97.0 Pa. After three weeks of reticulation and a finished self-setting process, a value of 343.2±106.5 Pa for the G' and a value of 44.5±15.4 Pa for the G" were observed.

MSC Viability and Activity in Three Dimensional Culture within Si-HPMC Hydrogel

To evaluate whether Si-HPMC hydrogel was cytotoxic, MSC viability was quantified in 3D culture in Si-HPMC by conventional fluorescent microscopy (data not shown). MSC viability was maintained during the whole culture period, from day 1 to day 7 (85.1±3.9% at day 1; 80.0±3.0% at day 2 and 74.3±3.9% at day 7; p=0.10 one-way ANOVA between groups) (FIG. 4).

To assess whether VEGF secretion was maintained in MSC 3D-cultured within Si-HPMC hydrogel for 7 days, VEGF concentrations were measured (ELISA) in supernatants at different time-points. Whereas VEGF concentrations in the control supernatants (MSCs cultured without hydrogel) were much higher (FIG. 5.A), VEGF concentration in supernatants from 3D-cultured MSCs within hydrogel increased overtime from 29.5±1.7 µg·ml$^{-1}$ at day 1 to 91.0±5.1 µg·ml-1 at day 2 to 181.2±6.4 µg·ml$^{-1}$ at day 7; $p<0.001$ for all comparisons) (FIG. 5.B).

Comparative Effects of Hydrogel, MSC, and MSC+Hydrogel on Cardiac Function and LV Remodeling MI was induced in 62 rats by ligation of the left anterior descending coronary artery. After MI induction, rats were randomised into 4 treatment groups to receive intramyocardial injections of (1) PBS as control, (2) Si-HPMC hydrogel alone (hydrogel), (3) MSCs alone (MSC) and (4) Si-HPMC hydrogel loaded with MSCs (MSC+hydrogel). Overall mortality at 24 hours after surgery was 30.7±7.7% (19/62 rats) with no significant differences between treatment groups (see below Table 1A). Echocardiography was performed 1 day after coronary ligation, to select rats with a significant myocardial infarction so as to maximize possible treatment effects (defined as animals with LVEF≤70%; table 1B). The number of selected rats was not significantly different between treatment groups (see below Table 1B). Importantly, parameters of left ventricular (LV) dimensions and function measured at day 1 were not different between the 4 treatment groups in the animals entering the echocardiography follow-up study (See below Table 2).

TABLE 1A

|  | Animals number at baseline | Living animals at day 1 |
|---|---|---|
| PBS | 11 | 10 |
| hydrogel | 14 | 11 |
| MSC | 15 | 9 |
| MSC + hydrogel | 22 | 13 |
| Total | 62 | 43 |

TABLE 1B

|  | Animals number with LVEF > 70% at day 1 | Animals number with LVEF < 70% at day 1 |
|---|---|---|
| PBS | 4 | 6 |
| hydrogel | 4 | 7 |
| MSC | 1 | 8 |
| MSC + hydrogel | 4 | 9 |
| Total | 13 | 30 |

TABLE 2

| Parameter | PBS (n = 6) | hydrogel (n = 7) | MSCs (n = 8) | MSC + hydrogel (n = 9) |
|---|---|---|---|---|
| LVEDD (mm) | | | | |
| Bsl | 5.4 ± 0.2 | 5.2 ± 0.2 | 5.6 ± 0.1 | 5.6 ± 0.2 |
| d1 | 5.9 ± 0.1 | 5.8 ± 0.3 | 6.2 ± 0.2 | 6.0 ± 0.1 |
| d7 | 6.6 ± 0.1 | 6.1 ± 0.3 | 6.3 ± 0.1 | 6.1 ± 0.2 |
| d28 | 7.2 ± 0.2 ¥ | 6.9 ± 0.3 ¥ | 7.0 ± 0.3 | 6.6 ± 0.3 |
| d56 | 7.4 ± 0.3 ¥ | 7.3 ± 0.5 ¥ | 7.0 ± 0.4 | 6.8 ± 0.2 |
| LVESD (mm) | | | | |
| Bsl | 2.4 ± 0.1 | 2.6 ± 0.2 | 2.8 ± 0.1 | 3.0 ± 0.2 |
| d1 | 4.0 ± 0.1 | 4.1 ± 0.3 | 4.3 ± 0.1 | 4.3 ± 0.2 |
| d7 | 5.0 ± 0.1 ¥ | 4.0 ± 0.3 * | 4.3 ± 0.2 * | 3.9 ± 0.2 * |
| d28 | 5.7 ± 0.3 ¥ | 5.0 ± 0.3 * | 5.2 ± 0.4 * | 4.3 ± 0.3 * |
| d56 | 6.0 ± 0.3 ¥ | 5.5 ± 0.5 * | 4.9 ± 0.3 * | 4.8 ± 0.1 * $ |
| FS (%) | | | | |
| Bsl | 56.6 ± 1.7 | 49.4 ± 2.0 | 49.5 ± 1.0 | 47.1 ± 2.2 |
| d1 | 29.0 ± 2.4 | 29.9 ± 2.8 | 30.4 ± 1.8 | 27.9 ± 1.9 |
| d7 | 24.1 ± 0.9 | 34.1 ± 2.0 * | 31.2 ± 2.5 | 36.9 ± 1.7 ¥ * + |
| d28 | 20.2 ± 2.3 | 28.0 ± 1.2 * | 26.7 ± 3.3 * | 34.4 ± 1.9 ¥ * + $ |
| d56 | 19.6 ± 1.5 | 25.6 ± 2.9 * | 30.8 ± 2.4 * | 29.4 ± 1.5 * $ |
| EF (%) | | | | |
| Bsl | 87.4 ± 1.5 | 86.0 ± 1.2 | 86.8 ± 1.9 | 88.2 ± 1.5 |
| d1 | 61.3 ± 4.0 | 64.6 ± 2.6 | 64.6 ± 1.8 | 61.2 ± 2.9 |
| d7 | 55.7 ± 2.4 | 68.0 ± 2.3 | 63.5 ± 3.2 | 76.0 ± 1.6 ¥ * + |
| d28 | 49.0 ± 2.5 | 71.7 ± 2.6 * | 72.4 ± 1.5 * | 76.4 ± 1.5 ¥ * |
| d56 | 47.4 ± 2.4 | 56.9 ± 4.6 | 65.4 ± 3.3 * | 68.5 ± 2.0 ¥ $ |

As expected in the PBS group, MI led to a time-dependent increase in LV chamber dimensions (LVEDD: 5.9±0.1 mm at day 1 vs 7.4±0.3 mm at day 56; p<0.05. LVESD: 4.0±0.1 mm at day 1 vs 6.0±0.3 mm at day 56; p<0.05.) (FIGS. 6.A and 6.B) and reduction in EF (61.3±1.5% at day 1 vs 47.4±2.4% at day 56; p<0.05) (FIG. 6.D) and fraction shortening (FS) (29.0±2.4% at day 1 vs 19.6±1.5% at day 56; p<0.001) (FIG. 6.C). As compared to PBS group injections of hydrogel, MSC or MSC+hydrogel significantly attenuated the MI-induced increase of LV end-systolic diameter (LVESD) (FIG. 6.B) and reduction of FS (FIG. 6.C) and EF (FIG. 6.D). Interestingly, significant differences were observed between these 3 groups:

(1) In the hydrogel groups, LVEF was significantly increased at 28 days after injection as compared to PBS group (71.7±2.6% vs 49.0±2.5%; p<0.001) but not at day 7 and day 56. In addition, the LVESD was reduced during the whole study as compared to PBS group but not the LVEDD. The LVESD, the LVFS and the LVEF were not significantly altered during the whole study as compared to day 1 but the LVEDD was increased at day 28 and 56 as compared to day 1 (7.3±0.5 mm at day 56 vs 5.8±0.3 mm at day 1; p<0.001).

(2) In the MSC group, LVEF was significantly increased at 28 and 56 days after injection as compared to PBS group (at day 56: 65.4±3.3% vs 47.4±2.4%; p<0.001), but not at day 7. In addition, the LVESD was reduced during the whole study as compared to PBS group but not the LVEDD. The LVESD, the LVEDD, the LVFS and the LVEF were not significantly altered during the whole study as compared to day 1.

(3) In the MSC+hydrogel group LVEF was significantly increased at day 7 up to day 56 after injection as compared to PBS group (at day 7: 76.0±1.6% vs 55.7±2.4%; p<0.001). In addition, the LVESD was reduced during the whole study as compared to PBS group but not the LVEDD. The LVFS and the LVEF were significantly increased compared to day 1 (61.2±2.9%) at 28 days (76.4±1.5%; p<0.001) then maintained at 56 days (68.5±2.0%; p=0.05).

Interestingly the LVEF was higher at day 7 as compared to LVEF in MSC group (76.0±1.6% vs 63.5±3.2%; p<0.05) and at day 56 in compared to hydrogel group (68.5±2.0% vs 56.9±4.6%; p<0.05). Similar results were observed for LVFS (FIG. 6C).

Comparative Effects of Hydrogel, MSC or MSC+Hydrogel on Infarct Expansion and Ventricular Fibrosis.

Morphometric analysis of heart sections was performed to analyse LV remodeling. For all animals, Infarct area was located in the anterior region of the left ventricle (FIG. 7A).

The MI size had been reduce as compared to the PBS group (53.8±2.5%) in the hydrogel group (43.0±4.2%; p<0.05), in the MSC group (35.2±1.5%; p<0.001) and in the MSC+hydrogel group (28.2±1.2%; p<0.001) (FIG. 7.B). In addition the MI size was reduced in MSC and MSC+hydrogel groups as compared to the hydrogel group.

The percentage of ventricular fibrosis (FIG. 7.C) was significantly reduced as compared to the PBS group (27.8±1.6%) in the hydrogel group (19.0±2.5%; p<0.05), MSC group (7.9±0.6%; p<0.001) and MSC+hydrogel group (6.7±0.6%; p<0.001).

Relative scar thickness (FIG. 8.B) was significantly increased as compared to PBS group (0.36±0.05) in hydrogel group (0.53±0.04; p<0.05), MSC group (0.59±0.04; p<0.05), and MSC+hydrogel group (0.63±0.04; p<0.001).

Infarct expansion index (FIG. 8.C) was significantly decreased as compared to PBS group (1.73±0.24) in hydrogel group (0.97±0.09; p<0.001), MSC group (0.81±0.04, p<0.001), and MSC+hydrogel (0.66±0.04; p<0.001).

Interestingly, chondroid metaplasia of the endocardium was observed in 83% rats in PBS group (FIG. 8.A) whereas this feature was visible in 67% rats in the hydrogel group, 60% rats in the MSC group, and only in 14% in rats in hydrogel+MSC groups.

Taken together, these results show that (1) hydrogel neither altered MSC viability nor activity and (2) injection of Si-HPMC hydrogel load with MSCs in the heart directly after MI leads to cardiac function and LV remodeling preservation as compared to hydrogel or MSCs alone.

The invention claimed is:

1. A method of treating heart failure including administration by injection into myocardium of an aqueous composition which has a physiological pH, said composition comprising:
   i) cardiomyocytes or stem cells which are able to differentiate into cardiomyocytes; and
   ii) a hydrogel solution comprising from 0.8 to 1.5% w/v of silylated-hydroxypropylmethylcellulose (Si-HPMC) capable of forming a pH dependent self-reticulating hydrogel.

2. The method according to claim 1, wherein the stem cells are mesenchymal stem cells.

3. The method according to claim 1, wherein the hydrogel solution (ii) has the following rheological characteristics at a pH value of 7.4 after 3 weeks of reticulation:
   a compressive modulus at 5% stress from 220 to 430 Pa;
   a storage modulus (G') from 235 to 450 Pa;
   a loss modulus (G") from 29 to 60 Pa;
   a gel point from 23.8 to 30.6 minutes.

4. A method of treating heart failure including administration by injection into myocardium of an aqueous composition which has a physiological pH, said composition comprising:
   i) cardiomyocytes or stem cells which are able to differentiate into cardiomyocytes; and
   ii) a hydrogel solution comprising silylated-hydroxypropylmethylcellulose (Si-HPMC), said Si-HPMC being capable of forming a pH dependent self-reticulating hydrogel,
   wherein the hydrogel solution has the following rheological characteristics at a pH value of 7.4 after 3 weeks of reticulation:
   a compressive modulus at 5% stress from 220 to 430 Pa;
   a storage modulus (G') from 235 to 450 Pa;
   a loss modulus (G") from 29 to 60 Pa;
   a gel point from 23.8 to 30.6 minutes.

* * * * *